US00PP08193P

United States Patent [19]

Moore

[11] Patent Number: Plant 8,193

[45] Date of Patent: Apr. 6, 1993

[54] MINIATURE ROSE PLANT NAMED 'MORALERT'

[75] Inventor: Ralph S. Moore, Visalia, Calif.

[73] Assignee: Sequoia Nursery, Visalia, Calif.

[21] Appl. No.: 803,227

[22] Filed: Dec. 6, 1991

[51] Int. Cl.[5] ..... A01H 5/00

[52] U.S. Cl. ..... Plt./10

[58] Field of Search ..... Plt. 10, 7.1

*Primary Examiner*—Howard J. Locker

[57] ABSTRACT

This invention relates to a new and distinct variety of miniature rose plant primarily identified by its medium red buds and flowers and hybrid tea form.

1 Drawing Sheet

1

The present invention relates to a new and distinct variety of hardy, dwarf, bush type rose plant of the miniature class; the variety being primarily characterized — as to novelty — by the buds and flowers of a uniform medium red color which generally are of exhibition (hybrid tea) form.

The variety is further characterized by:

An abundance of bloom, with flowers often borne singly and also several to the stem in loose clusters.

Slight fragrance.

A plant which is vigorous, of rounded, upright shape with medium size, semi-glossy to matte foliage with pointed leaflets the buds and flowers being similar in form and size to Starina (miniature — U.S. Plant Pat. No. 2,646).

The plant, which has a normal height of 12–14 inches or more, can easily be maintained at lesser height by occasional trimming.

A plant which grows and blooms satisfactorily both in greenhouse and outdoors; is good for growing in pots; and provides excellent garden decoration as well as cut flowers.

The present variety of miniature rose was originated by me at my nursery located at Visalia, Calif., under conditions of careful control and observation, as a cross between Orangeade (Florabunda — not patented) as the seed parent and Rainbow's End (miniature — U.S. Plant Pat. No. 5,482) as the pollen parent.

Subsequently to origination of the variety I successfully asexually reproduced it at the same nursery, located as aforesaid, by budding as well as by cuttings; the reproductions having run true in all respects.

The color photograph illustrates the variety, including the foliage, buds and flowers.

Referring now specifically to the new and distinct variety of miniature rose plant, the following is a detailed description thereof in outline; all major color plate identifications being by reference to the British Colour Council Horticultural Colour Chart, except where common terms of color definition are employed.

Type: Hardy; dwarf; bushy; upright; seedling; greenhouse; outdoors; cut flowers; garden decoration; potted plant.

Class: Miniature. Variety identification: MORalert (Commercial synonym: RED ALERT).

Flowers borne: Singly and several together on slender wirey stems.

Quantity of bloom: Abundant both outside and in greenhouse.

2

Bud:

*Sepals.*—Permanent; spear-shaped; recurved.

*Peduncle.*—Medium to long; slender but sturdy; erect; medium to light green, sometimes tinted bronze (outdoors); with no prickles and numerous very short hairs.

*Before calyx breaks.*—Size — small. Form long; pointed with several foliaceous apendages on surface of bud; with foliaceous parts extending beyond the tip of the bud equal to one-half or more of its length. Color — medium green, occasionally tinted with bronze (outdoors).

*As calyx breaks.*—Color — red, often whitish at base.

*Opening.*—Opens well in all weather.

Bloom:

*Size when fully open.*—Small, averaging about 40 mm (1⅝").

*Petalage.*—Double—averaging about 35–40 petals, arranged regularly plus several small petaloids.

*Form.*—High centered with petals rolled loosely outward and downward. Open flowers may show stamens.

Petals: Fairly thick; velvety on inside and satiny on outside surface.

*Shape.*—Outside petals, broad lanceolate with rounded tip; Intermediate — broad lanceolate with small acute tip; Inside — lanceolate with acute tip.

Color: Newly opened flower from a plant grown in plastic greenhouse (September, 1991), Visalia, Calif.:

*Outside petal.*—Outside surface—near Rose Red 724/1 with very fine darker veining, becoming whitish near base. Inside surface—near Cardinal Red 822 (with orangish under tones) becoming whitish at base.

*Intermediate petal.*—Outside surface similar to outside petal. Inside surface similar to outside petal.

*Inner petal.*—Outside surface — same as intermediate petal; inside surface — same as intermediate petal. General color effect; Buds and newly opened flowers — coral red with darker reverse. NOTE: Color can vary slightly, depending upon weather, time of year, light intensity, etc., — the orangish undertone of newly opened flowers may vary giving the flower a slightly different "color effect". Three days open — color — similar to newly opened flowers, but lighter color. Behavior — opens well in all weather. Spent petals drop off.

Flower longevity (September 1991): Plant in pot 6–8 days or longer. Cut flowers at living room temperature 4–5 days or longer.

Reproductive organs:

*Stamens.*—Arranged regularly about pistils.

*Filaments.*—Varying length, short to medium long, Yellow.

*Anthers.*—Well formed; yellow.

*Pollen.*—Some.

*Pistils.*—Average number.

*Styles.*—Varying length—medium long; reddish; bunched.

*Stigmas.*—Whitish.

*Ovaries.*—All enclosed in calyx.

*Hips.*—None.

*Seed.*—None.

Foliage:

*Leaves.*—Compound of five (sometimes three or seven) leaflets; medium size; leathery; semi-glossy to matte.

*Leaflets.*—Shape: broad; fairly short; nearly oval; apex acute; base rounded. Color: medium green; new growth — normal (medium) green (sometimes tinted reddish). Rachis: medium strength; upper side may have a few short hairs; grooved; underside may have several thorns (1 to 3) and few or no tiny prickles or hairs. Stipules: medium to short length; medium width; short to medium length narrow points which turn out usually at about 45 degrees or more.

Growth:

*Habit.*—Dwarf; bushy; upright; much branched.

*Growth.*—Free; vigorous; internodes short.

*Canes.*—Medium; slender; sturdy.

*Main stems.*—Color: medium green.

*Thorns.*—Several, medium to long, usually thin and straight. Prickles — none. Hairs — none.

*Branches.*—Color: medium green. Thorns: several; slender; medium to long—straight. Prickles: none. Hairs — none.

The miniature rose plant and its flowers as herein described may vary in slight detail due to climatic, soil and cultural conditions under which the variety may be grown; the present description being of the variety as grown at Visalia, Calif.

The following is claimed:

1. A new and distinct variety of miniature rose plant of hardy, dwarf, bushy, upright, much branched habit, substantially as illustrated and described, characterized by buds and flowers of exhibition form, essentially medium red in color, with reverse of petals being a slightly lighter shade of red, and further characterized by the being plant of compact well rounded shape, vigorous, with the main stems and shoots being moderately thorny, said plant being easy to propagate from cuttings or by budding, with an abundance of flowers borne singly or several to the stem in loose clusters.

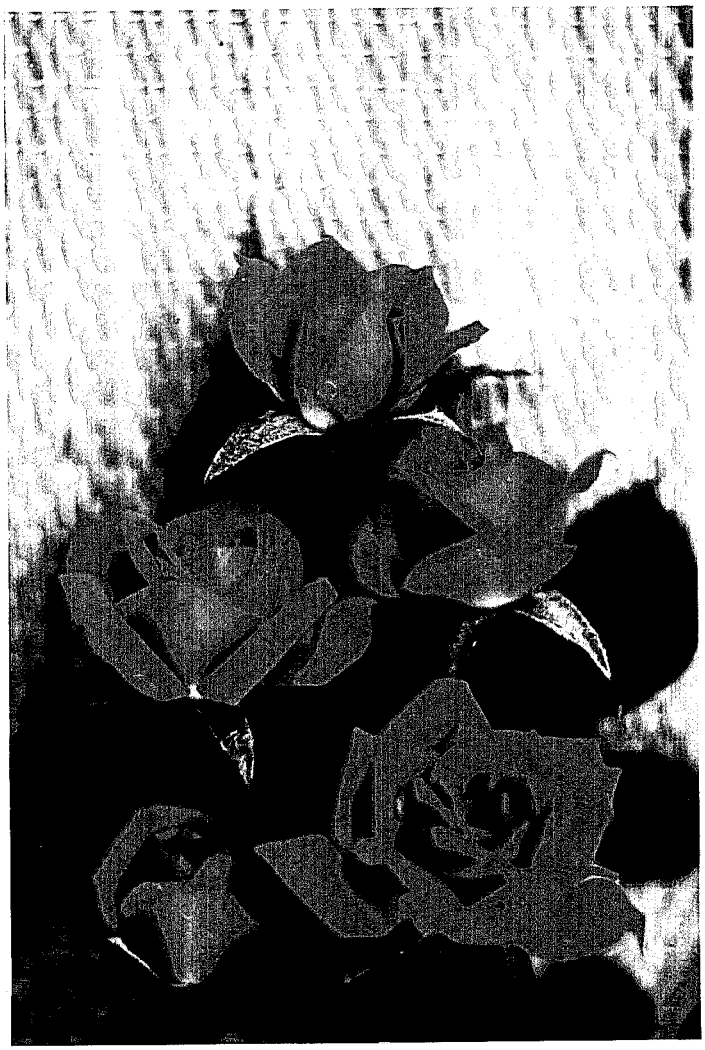

* * * * *